(12) United States Patent
Schwarz

(10) Patent No.: US 6,746,572 B2
(45) Date of Patent: Jun. 8, 2004

(54) METHOD FOR DETERMINING A CHARACTERISTIC VALUE FOR THE BINDING FORCE POTENTIAL OF SUSPENDED PAPER FIBERS AND USE OF THIS METHOD

(75) Inventor: Michael Schwarz, Heidenheim (DE)

(73) Assignee: Voith Paper Patent GmbH, Heidenheim (DE)

(*) Notice: Subject to any disclaimer, the term of this patent is extended or adjusted under 35 U.S.C. 154(b) by 0 days.

(21) Appl. No.: 10/169,370
(22) PCT Filed: Jan. 13, 2001
(86) PCT No.: PCT/EP01/00385
§ 371 (c)(1),
(2), (4) Date: Jul. 1, 2002
(87) PCT Pub. No.: WO01/55501
PCT Pub. Date: Aug. 2, 2001

(65) Prior Publication Data
US 2003/0000670 A1 Jan. 2, 2003

(30) Foreign Application Priority Data
Jan. 26, 2000 (DE) .......................................... 100 03 383

(51) Int. Cl.⁷ ............................. D21F 1/06; D21F 7/00; G01N 7/00
(52) U.S. Cl. ........................ 162/198; 162/216; 162/254; 162/262; 162/263; 162/336; 162/380; 73/19.01; 73/53.03
(58) Field of Search .......................... 162/49, 458, 198, 162/199, 216, 252–254, 259, 262, 263, 264, 272, 336, 380, DIG. 10, DIG. 11; 73/19.01, 19.1, 19.05, 53.01, 53.03, 53.04; 95/1, 23; 96/156, 176

(56) References Cited

U.S. PATENT DOCUMENTS

| 4,952,280 A | 8/1990 | Hemel et al. |
| 5,891,307 A | 4/1999 | Graf |

FOREIGN PATENT DOCUMENTS

| EP | 0349860 | 1/1990 |
| WO | 99/53137 | 10/1999 |

OTHER PUBLICATIONS

Matula, Jouni P. and Kukkamaki, Esko, "New findings of entrained air and dissolved gases in PM wet end: A mill case study", TAPPI Journal, Apr. 2000, pp. 66–67.*

Pietikainen, Tapio, "On–line air entrainment tests on paper machines", TAPPI Journal, Nov. 1992, pp. 185–191.*

Kortelainen, Helena, "Tools for successful wet–end chemistry control", TAPPI Journal, Dec. 1992, pp. 112–117.*

Karras, Matti et al., "Ultrasonic measurement of gaseous air in pulp suspensions", TAPPI Journal, Jan. 1988, pp. 65–69.*

* cited by examiner

Primary Examiner—Steven P. Griffin
Assistant Examiner—Eric Hug
(74) Attorney, Agent, or Firm—Greenblum & Bernstein, P.L.C.

(57) ABSTRACT

Method for determining a characteristic value for a binding force potential of paper fibers in a fibrous suspension. The method includes measuring an air content of the fibrous suspension and deriving the characteristic value from the measuring.

38 Claims, 1 Drawing Sheet

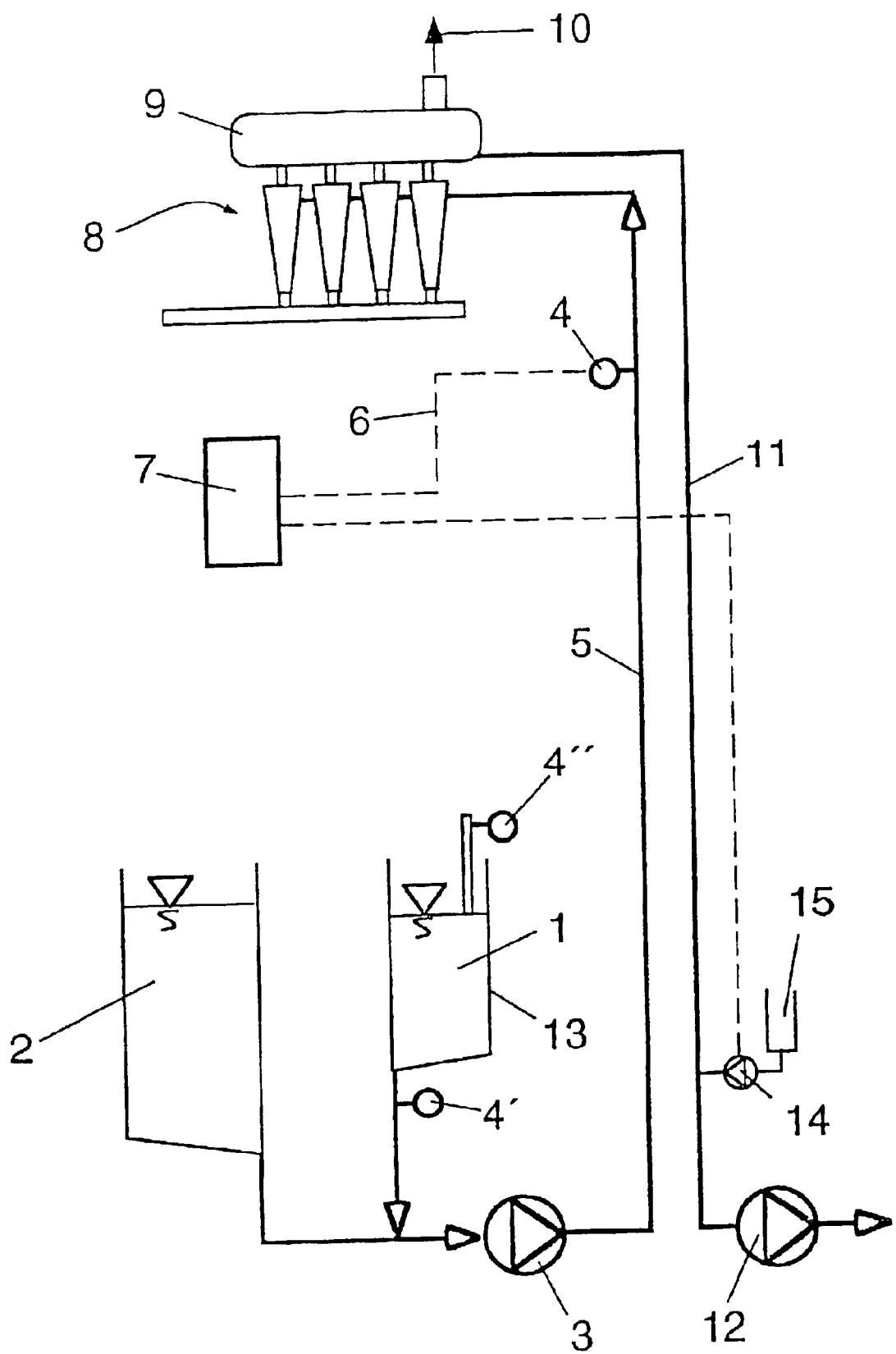

METHOD FOR DETERMINING A CHARACTERISTIC VALUE FOR THE BINDING FORCE POTENTIAL OF SUSPENDED PAPER FIBERS AND USE OF THIS METHOD

CROSS-REFERENCE TO RELATED APPLICATIONS

The present application is a National Stage Application of International Application No. PCT/EP01/00385, filed Jan. 13, 2001. Further, the present application claims priority under 35 U.S.C. § 119 of German Patent Application No. DE 100 03 383.0 filed on Jan. 26, 2000.

BACKGROUND OF THE INVENTION

1. Field of the Invention

The invention relates to a method for determining a characteristic value for the binding force potential of paper fibers in a fibrous suspension prepared for paper manufacture.

2. Discussion of Background Information

In paper manufacture it is known that paper fibers are placed in an aqueous fibrous suspension on the paper machine and dewatered. The paper fibers touching each other thereby develop binding forces which ultimately lead to the formation of a firmly cohesive sheet of paper. The possibility of developing such binding forces, i.e., the binding force potential, depends on a plurality of parameters. The most important are fiber condition and fiber size, as well as the chemical and material environment in the suspension. Improving the binding force potential is often associated with costs for raw material quality, processing and the use of chemical aids. It is therefore desirable to be able to determine the binding force potential in a timely manner, i.e., before the actual paper production, so as to be able to optimize the entire process.

SUMMARY OF THE INVENTION

The invention therefore provides for a method in which the binding force potential of paper fibers in an aqueous suspension can be characterized. In particular, the invention makes possible the detection of deviations from the desired binding force potential in a timely manner. The measurement leads to quick measurement readings.

According to one embodiment, there is provided a method for determining a characteristic value for the binding force potential of paper fibers in a fibrous suspension prepared for paper manufacture, characterized in that the air content of the fibrous suspension is measured and that the characteristic value is derived therefrom.

The air content can be measured at a measuring point in the fiber stock preparation process at which the fibrous suspension has the stock composition necessary for paper manufacture, without the air content having been adjusted by a corresponding deaeration process. The air content can be measured in the approach flow system of a paper mill after the mixing pump in which the fiber stock is mixed with diluting water. The air content in the approach flow system of a paper mill can be measured before the mixing pump in which the fiber stock is mixed with diluting water. After measuring the air content, the fibrous suspension can be deaerated by way of a vacuum. Several sorts of fiber stock can be used for paper manufacture at the same time, and that the air content can be measured separately in the sorts. The characteristic value for the binding force potential can be assigned to the air content with the aid of corresponding empirical values. The empirical values can be determined by measuring the strengths of the sheets formed from the suspension. The empirical values can be assigned to the paper machine by determining the runability achieved with the fibrous suspension. An amount of strengthening chemicals and/or retention agents added to the fibrous suspension can be adjusted such that a characteristic value which was stipulated as useful is maintained. The amount of strengthening chemicals and/or retention agents added to the fibrous suspension can be minimized according to the demands on runability.

Particularly useful measuring data are obtained at the point where no measures have yet been taken for the effective deaeration of the fibrous suspension. Here, the air content can freely adjust according to the fiber technology and chemical parameters of the fiber stock prepared for paper manufacture. Surprisingly, the correlation of the air content measured at this point and the binding force potential can be defined with sufficient accuracy that an early prediction can be made of certain paper properties to be expected. This correlation can be easily determined, e.g., by way of empirical measurements even without all causalities being known. It can be assumed that the air content itself is not important for binding force potential, but it serves merely as an indicator. In many cases a higher binding force potential can be established with a higher air content.

In practice the air content measurement is made, e.g., in the approach flow system of the paper mill after the mixing pump in which the paper stock is mixed with the diluting water and brought to the required stock consistency. If the paper or cardboard is to be produced from different sorts, the characteristic values for these sorts can also be separately determined and corrections made individually.

Various possibilities are conceivable for reacting to the deviation of the characteristic value from its set value: the use of chemical agents, changing the fiber treatment or composition or adjusting the paper machine up to reducing the wire speed.

With the aid of the method according to the invention, the paper machine process can be brought up to optimum runability on the paper machine simply and economically. It makes it possible to correct the binding force potential in a timely manner, i.e., before a break has occurred on the paper machine. It is known that the prevention of breaks is a very important economic advantage in paper manufacture.

The invention also provides for a method for determining a characteristic value for a binding force potential of paper fibers in a fibrous suspension, the method comprising measuring an air content of the fibrous suspension and deriving the characteristic value from the measuring.

The method may further comprise feeding the fibrous suspension to a paper machine. The measuring may comprise measuring the air content at a measuring point arranged before the fibrous suspension is fed to a paper machine. The method may further comprise subjecting the fibrous suspension to deaeration. The measuring may comprise measuring the air content at a measuring point arranged before the fibrous suspension is subjected to deaeration. The measuring may occur at a point in an approach flow system of a paper mill. The point may be arranged downstream of a mixing pump that mixes a fiber stock with diluting water. After the measuring, the method may further comprise deaerating the fibrous suspension using a vacuum. The measuring may comprise measuring an air content of the fibrous suspension of each of several sorts of fiber stock. The measuring an air content of the fibrous suspension of each of several sorts of fiber stock may occur at the same time. The measuring an air content of the fibrous suspension of each of several sorts of fiber stock may occur separately.

The method may further comprise assigning the characteristic value to the air content using corresponding empirical values. The method may further comprise determining the empirical values by measuring strengths of sheets formed from the fibrous suspension. The method may further comprise determining a runability of the fibrous suspension and assigning the empirical values to a paper machine based upon the determining. The method may further comprise adding an amount of strengthening chemicals and/or retention agents to the fibrous suspension. The method may further comprise adjusting the amount of strengthening chemicals and/or retention agents based upon the characteristic value. The method may further comprise maintaining the amount of strengthening chemicals and/or retention agents based upon the characteristic value. The method may further comprise minimizing the amount of strengthening chemicals and/or retention agents added to the fibrous suspension. The method may further comprise determining a runability and minimizing an amount of strengthening chemicals and/or retention agents added to the fibrous suspension based upon the runability.

The invention also provides for a method for determining a characteristic value for a binding force potential of paper fibers in a fibrous suspension, the method comprising feeding the fibrous suspension to a paper machine, measuring an air content of the fibrous suspension before the feeding, and controlling the characteristic value based upon the measuring.

The method may further comprise forming the fibrous suspension by mixing prepared fiber stock and water. The water may comprise backwater from a paper machine. The measuring may comprise measuring the air content at a measuring point arranged before the fibrous suspension is fed to a deaeration device. The method may further comprise, after the measuring, subjecting the fibrous suspension to deaeration. The measuring may comprise measuring the air content of a prepared fiber stock. The measuring may comprise measuring the air content of a sample of prepared fiber stock. The measuring may comprise measuring the air content after the fibrous suspension is formed by mixing a prepared fiber stock with water and before the fibrous suspension is subjected to deaeration. The measuring may occur at a point in an approach flow system of a paper mill. The point may be arranged downstream of a mixing pump that mixes a fiber stock with diluting water. After the measuring, the method may further comprise deaerating the fibrous suspension using vacuum.

The method may further comprise controlling a proportioning pump using a regulator which is connected to a measuring point via a signal line. The method may further comprise determining empirical values by measuring strengths of sheets formed from the fibrous suspension. The method may further comprise determining a runability of the fibrous suspension and assigning the empirical values to a paper machine based upon the determining. The method may further comprise regulating an amount of strengthening chemicals and/or retention agents added to the fibrous suspension. The method may further comprise adjusting the amount of strengthening chemicals and/or retention agents based upon the measuring. The method may further comprise maintaining the amount of strengthening chemicals and/or retention agents based upon the measuring. The method may further comprise minimizing an amount of strengthening chemicals and/or retention agents added to the fibrous suspension based upon the measuring. The method may further comprise determining a runability and minimizing an amount of strengthening chemicals and/or retention agents added to the fibrous suspension based upon the runability.

The invention still further provides for a system for determining a characteristic value for a binding force potential of paper fibers in a fibrous suspension, the system comprising a mixing device which mixes a prepared fiber stock and water to form the fibrous suspension, a deaeration device which removes air from the fibrous suspension, a measuring device which measures an air content of the fibrous suspension before the deaeration device, and a regulator connected to the measuring device and a proportioning pump.

BRIEF DESCRIPTION OF THE DRAWINGS

The FIGURE shows an arrangement by which the invention can be practiced.

DETAILED DESCRIPTION OF THE INVENTION

In the FIGURE it can be seen that the already prepared fiber stock 1 is mixed with the diluting water 2, which originates from, e.g., the back water of the paper machine, in the mixing pump 3. A fibrous suspension is thus formed which has the stock consistency which is provided for the operation of the paper machine. In the example shown here, this fibrous suspension first arrives via a feedpipe 5 at a cleaner battery 8 and then at a deaeration container 9. The feedpipe 5 brings the fibrous suspension to a higher geodetical level, which facilitates deaeration by vacuum. It is known that the cleaner battery 8 is used for the precipitation of fine heavy parts, and the deaeration container 9 for removing the air 10 from the suspension with the aid of vacuum. Such and similar treatment steps are known per se, and so just this one possibility is shown diagrammatically. In connection with the method according to the invention, it is advantageous if the measuring point 4, at which the air content measurement is made, is located where the deaeration of the fibrous suspension has not yet been carried out. From measuring point 4 a regulator 7 is controlled via a signal line 6, which regulator can trigger the corrections or control actions described above. As shown here by way of example, this can be the control of a proportioning pump 14 with which a chemical retention agent 15 is added to the suspension. Alternatively, this FIGURE shows two other measuring points at which the as yet undiluted fiber stock 1 is measured, e.g., in the drain pipe of the corresponding vat 13 (measuring point 4') or with a stock sample taken from the vat 13 (measuring point 4").

The cleaned and deaerated fibrous suspension is guided through an outlet pipe 11 to the pump 12 from which it can reach, e.g., the proportioning system or the headbox of a paper machine. The proportioning system is used e.g. for mixing different components used in paper manufacture.

What is claimed is:

1. A method for determining a characteristic value for a binding force potential of paper fibers in a fibrous suspension, the method comprising:

measuring an air content of the fibrous suspension; and deriving the characteristic value from the measuring, wherein the measuring comprises measuring the air content at a measuring point arranged before the fibrous suspension is subjected to deaeration.

2. The method of claim 1, further comprising feeding the fibrous suspension to a paper machine.

3. The method of claim 1, wherein the measuring comprises measuring the air content at a measuring point arranged before the fibrous suspension is fed to a paper machine.

4. The method of claim 1, wherein the measuring occurs at a point in an approach flow system of a paper mill.

5. The method of claim 4, wherein the point is arranged downstream of a mixing pump that mixes a fiber stock with diluting water.

6. The method of claim 1, wherein after the measuring, the the fibrous suspension is subjected to deaeration using a vacuum.

7. The method of claim 1, wherein the measuring comprises measuring an air content of the fibrous suspension of each of several sorts of fiber stock.

8. The method of claim 7, wherein the measuring of an air content of the fibrous suspension of each of several sorts of fiber stock occurs at the same time.

9. The method of claim 7, wherein the measuring of an air content of the fibrous suspension of each of several sorts of fiber stock occurs separately.

10. The method of claim 1, further comprising assigning the characteristic value to the air content using corresponding empirical values.

11. The method of claim 10, further comprising determining the empirical values by measuring strengths of sheets formed from the fibrous suspension.

12. The method of claim 10, further comprising determining a runability of the fibrous suspension and assigning the empirical values to a paper machine based upon the determining.

13. The method of claim 1, further comprising adding an amount of strengthening chemicals and/or retention agents to the fibrous suspension.

14. The method of claim 13, further comprising adjusting the amount of strengthening chemicals and/or retention agents based upon the characteristic value.

15. The method of claim 13, further comprising maintaining the amount of strengthening chemicals and/or retention agents based upon the characteristic value.

16. The method of claim 13, further comprising minimizing the amount of strengthening chemicals and/or retention agents added to the fibrous suspension.

17. The method of claim 16, further comprising determining a runability and minimizing an amount of strengthening chemicals and/or retention agents added to the fibrous suspension based upon the runability.

18. A method for determining a characteristic value for a binding force potential of paper fibers in a fibrous suspension, the method comprising:

measuring an air content of the fibrous suspension;

deriving the characteristic value from the measuring; and correcting a deviation of the characteristic value, wherein the measuring and correcting occurs before the fibrous suspension is fed to a headbox of a paper machine.

19. A method for determining a characteristic value for a binding force potential of paper fibers in a fibrous suspension, the method comprising:

feeding the fibrous suspension to a paper machine;

measuring an air content of the fibrous suspension before the feeding; and controlling the characteristic value based upon the measuring, wherein the measuring and the controlling occurs before the fibrous suspension is fed to the paper machine.

20. The method of claim 19, further comprising forming the fibrous suspension by mixing prepared fiber stock and water.

21. The method of claim 20, wherein the water comprises backwater from a paper machine.

22. The method of claim 19, wherein the measuring comprises measuring the air content at a measuring point arranged before the fibrous suspension is fed to a deaeration device.

23. The method of claim 19, further comprising subjecting the fibrous suspension to deaeration after the measuring.

24. The method of claim 23, wherein the measuring comprises measuring the air content of a prepared fiber stock.

25. The method of claim 23, wherein the measuring comprises measuring the air content of a sample of prepared fiber stock.

26. The method of claim 23, wherein the measuring comprises measuring the air content after the fibrous suspension is formed by mixing a prepared fiber stock with water and before the fibrous suspension is subjected to deaeration.

27. The method of claim 19, wherein the measuring occurs at a point in an approach flow system of a paper mill.

28. The method of claim 27, wherein the point is arranged downstream of a mixing pump that mixes a fiber stock with diluting water.

29. The method of claim 19, wherein after the measuring, the method further comprises deaerating the fibrous suspension using vacuum.

30. The method of claim 19, further comprising controlling a proportioning pump using a regulator which is connected to a measuring point via a signal line.

31. The method of claim 19, further comprising determining empirical values by measuring strengths of sheets formed from the fibrous suspension.

32. The method of claim 31, further comprising determining a runability of the fibrous suspension and assigning the empirical values to a paper machine based upon the determining.

33. The method of claim 19, further comprising regulating an amount of strengthening chemicals and/or retention agents added to the fibrous suspension.

34. The method of claim 19, further comprising adjusting the amount of strengthening chemicals and/or retention agents based upon the measuring.

35. The method of claim 34, further comprising maintaining the amount of strengthening chemicals and/or retention agents based upon the measuring.

36. The method of claim 19, further comprising minimizing an amount of strengthening chemicals and/or retention agents added to the fibrous suspension based upon the measuring.

37. The method of claim 19, further comprising determining a runability and minimizing an amount of strengthening chemicals and/or retention agents added to the fibrous suspension based upon the runability.

38. A system for determining a characteristic value for a binding force potential of paper fibers in a fibrous suspension, the system comprising:

a mixing device which mixes a prepared fiber stock and water to form the fibrous suspension;

a deaeration device which removes air from the fibrous suspension;

a measuring device which measures an air content of the fibrous suspension before the deaeration device;

a proportioning pump; and a regulator connected to the measuring device and the proportioning pump, wherein the system determines the characteristic value for a binding force potential.

* * * * *